United States Patent [19]

Ito

[11] Patent Number: 5,049,746
[45] Date of Patent: Sep. 17, 1991

[54] METHOD AND APPARATUS FOR DISPLAYING ENERGY SUBTRACTION IMAGES

[75] Inventor: Wataru Ito, Kanagawa, Japan

[73] Assignee: Fuji Photo Film Co., Ltd., Kanagawa, Japan

[21] Appl. No.: 599,924

[22] Filed: Oct. 19, 1990

[30] Foreign Application Priority Data

Oct. 19, 1989 [JP] Japan .................................. 1-272219
Jan. 17, 1990 [JP] Japan ...................................... 2-7335
Apr. 4, 1990 [JP] Japan .................................... 2-89370

[51] Int. Cl.$^5$ .......................................... G06F 15/42
[52] U.S. Cl. .................................. 250/327.2; 378/62; 378/99; 364/413.23
[58] Field of Search ................. 250/327.2 C, 327.2 D, 250/327.2 G, 327.2 B; 378/53, 54, 62, 94; 358/111; 364/413.23

[56] References Cited

U.S. PATENT DOCUMENTS

| | | | |
|---|---|---|---|
| 3,904,874 | 9/1975 | Amtmann et al. | 378/99 |
| 4,258,264 | 3/1981 | Kotera et al. | |
| 4,551,800 | 11/1985 | Riederer et al. | 364/414 |
| 4,590,517 | 5/1986 | Kato et al. | |
| 4,792,900 | 12/1988 | Sones et al. | 364/413.23 |
| 4,819,188 | 4/1989 | Matsubara et al. | 364/413.23 |
| 4,855,598 | 8/1989 | Ohgoda et al. | |

*Primary Examiner*—Constantine Hannaher
*Assistant Examiner*—Edward J. Glick
*Attorney, Agent, or Firm*—Sughrue, Mion, Zinn, Macpeak & Seas

[57] ABSTRACT

Digital image signals are detected from radiation images of an object constituted of bones and soft tissues, which radiation images have been formed with at least two kinds of radiation having different energy distributions and having passed through the object and in which different images of at least part of the object are embedded. A substraction process is carried out on the digital image signals, and a difference signal representing a soft tissue image and a difference signal representing a bone image are obtained. Different image processing operations are carried out on the difference signal representing the soft tissue image and the difference signal representing the bone image. The difference signals, which have been obtained from the image processing operations, are then added together. A visible radiation image of the object is reproduced from an image signal, which has been obtained from the addition.

14 Claims, 3 Drawing Sheets

METHOD AND APPARATUS FOR DISPLAYING ENERGY SUBTRACTION IMAGES

BACKGROUND OF THE INVENTION

1. Field of the Invention

This invention relates to a method for displaying an energy subtraction image obtained from subtraction processing, in particular, digital subtraction processing, which is carried out on radiation images, and an apparatus for carrying out the method.

2. Description of the Prior Art

Techniques for carrying out digital subtraction processing on radiation images have heretofore been known. When digital subtraction processing is to be carried out, two radiation images recorded under different conditions are photoelectrically read out, and digital image signals which represent the radiation images are obtained. The image signal components of the digital image signals which represent corresponding picture elements in the radiation images are then subtracted from each other, and a difference signal is thereby obtained which represents the image of a specific structure or part of the object represented by the radiation images. With the subtraction processing method, two digital image signals are subtracted from each other in order to obtain a difference signal, and the radiation image of a specific structure can be reproduced from the difference signal.

Basically, subtraction processing is carried out with either the so-called temporal (time difference) subtraction processing method or the so-called energy subtraction processing method. In the former method, in order to extract the image of a specific structure of an object from the image of the whole object, the image signal representing a radiation image obtained without injection of contrast media is subtracted from the image signal representing a radiation image in which the image of the specific structure of the object is enhanced by the injection of contrast media. In the latter method, such characteristics are utilized that a specific structure of an object exhibits specific radiation energy absorbing characteristics. Specifically, an object is exposed to several kinds of radiation with different energy distributions. In this manner, two radiation images, in which different images of a specific structure are embedded, are obtained. Thereafter, the image signals representing the two radiation images are weighted appropriately, and the weighted image signals are subjected to a subtraction process. The image of the specific structure is thereby extracted.

Subtraction processing is extremely effective, particularly for medical diagnosis utilizing image processing of X-ray images, and electronics research has continued to develop improved subtraction processing methods.

By storing radiation images of an object, which is constituted of bones and soft tissues, on two stimulable phosphor sheets and carrying out energy subtraction processing on image signals representing the radiation images, a subtraction image can be obtained in which the patterns of the bones have been erased and only the patterns of the soft tissues have been extracted. (Such a subtraction image will hereinbelow be referred to as the "soft tissue image".) Alternatively, a subtraction image can be obtained in which the patterns of the soft tissues have been erased and only the patterns of the bones have been extracted. (Such a subtraction image will hereinbelow be referred to as the "bone image".) However, in such cases, the soft tissue image or the bone image can only be observed independently.

With an image (e.g. an image of the chest of a human body) including both the bone patterns and the soft tissue patterns, both patterns can be observed simultaneously. For medical diagnosis, such an image is convenient from the point of view in that, for example, the relationship between the positions of the bone patterns and the soft tissue patterns can be found easily.

Also, a need exists for an image which has good image quality and can serve as an effective tool in, particularly, the efficient and accurate diagnosis of an illness. Such an image can be obtained by carrying out energy subtraction processing, generating an image signal representing only a soft tissue image or a bone image, and thereafter carrying out an image processing operation in a manner suitable for the image signal. For example, it is also desired that, only the patterns of edges or ridges of bones be emphasized in a bone image, or that only the patterns of interstitial tissues be emphasized in a soft tissue image.

Therefore, it will be very advantageous for diagnosis if image processing operations can be carried out independently on the image signal representing a bone image and the image signal representing a soft tissue image, and an image can be displayed in which the bone image and the soft tissue image are superposed one upon the other. For example, it will be very convenient for diagnosis if an image can be displayed in which only the patterns of edges or ridges of bones are emphasized, while patterns of blood vessels, or the like, are not particularly emphasized, or if an image can be displayed in which the patterns of bones are unsharp and only the patterns of interstitial tissues, such as the lung fields, are emphasized.

SUMMARY OF THE INVENTION

The primary object of the present invention is to provide a method for displaying an energy subtraction image wherein image processing operations suitable for a bone image and a soft tissue image, which have been obtained from energy subtraction processing, are independently carried out on the bone image and the soft tissue image, and thereafter a single image is displayed, in which the processed bone image and the processed soft tissue image are superposed one upon the other.

Another object of the present invention is to provide a method for displaying an energy subtraction image wherein an image is displayed which has good image quality and can serve as an effective tool in, particularly, the efficient and accurate diagnosis of an illness.

The specific object of the present invention is to provide an apparatus for carrying out the method for displaying an energy subtraction image.

The present invention provides a method for displaying an energy subtraction image during energy subtraction processing wherein a plurality of radiation images of an object constituted of bones and soft tissues, which radiation images have been formed with at least two kinds of radiation having different energy distributions and having passed through the object and in which different images of at least part of the object are embedded, are read out and converted into a plurality of digital image signals, each of which is made up of a series of image signal components, the image signal components of the digital image signals which represent corresponding picture elements in the plurality of the radiation images are then subtracted from each other, and a difference signal representing a soft tissue image, in which the patterns of the bones represented by the radiation images have been erased, and a difference signal representing a bone image, in which the patterns of the soft tissues represented by the radiation images have been erased, are thereby obtained, the method for displaying an energy subtraction image comprising the steps of:

i) carrying out different image processing operations on said difference signal representing said soft tissue image and said difference signal representing said bone image, ii) adding the difference signals, which have been obtained from said image processing operations, and iii) reproducing a visible radiation image of said object from an image signal, which has been obtained from said addition.

In the method for displaying an energy subtraction image in accordance with the present invention, different image processing operations are carried out on the difference signal representing the soft tissue image and the difference signal representing the bone image. The term "carrying out different image processing operations" as used herein embraces the cases wherein different image processing operations are positively carried out on both difference signals and the cases wherein an image processing operation is carried out only on one of the difference signals, while no image processing operation is carried out on the other difference signal.

As the image processing operations, various types of image processing operations may be employed. For example, frequency emphasis processing operations, gradation processing operations, or the like, may be employed. In cases where completely different frequency emphasis processing operations are carried out on the soft tissue image and the bone image, it often occurs that the graininess of the two images becomes unbalanced, and an image is obtained which contains much noise and is visually difficult to read. Therefore, when different frequency emphasis processing operations are carried out on the soft tissue image and the bone image, operations should preferably carried out wherein emphasis coefficients are equal and only the mask sizes are different. In such cases, frequency emphasis processing can be carried out in different ways for the images of the structures of the object having different radiation absorption coefficients such that much noise does not occur in a resulting image. Also, the image, which has been processed with a larger mask size, becomes buoyant in the resulting image, and the image, which has been processed with a smaller mask size, becomes depressed in the resulting image.

Graininess, which is visually perceived in an image, is primarily caused by frequency components falling within the high frequency range. Therefore, noise can be rendered imperceptible by using an equal emphasis coefficient for the frequency components falling within the high frequency range.

The frequency emphasis processing can be expressed as $$S = Sorg + \beta(Sorg - Sus) \quad (1)$$

wherein S denotes an emphasized image signal, Sorg denotes an original image signal which is subjected to the frequency emphasis processing, $\beta$ denotes the emphasis coefficient, and Sus denotes an unsharp mask signal. The term "mask size" as used herein means the size of a mask, which is used when the unsharp mask signal Sus is generated. The unsharp mask signal Sus represents the mean value of the values of image signal components representing $N^2$ number of picture elements, i.e. a group of picture elements arrayed along N number of rows and N number of columns. The mask size means the size of the square part of the image which part is composed of the group of picture elements arrayed along N number of rows and N number of columns.

In cases where patterns appearing in the soft tissue image are to be observed primarily, it is desirable that positions of bone patterns can be found simultaneously. In order for this requirement to be satisfied, as the image processing carried out on the difference signal representing the bone image or as part of the image processing, a process should preferably be carried out such that noise components contained in the bone image are kept and the contrast of the bone patterns is decreased. As such a process, by way of example, a process may be employed wherein the bone image is separated into the noise components and a bone image containing no noise component by being subjected to nonlinear filtering processing, the contrast of the bone image containing no noise component is decreased, and thereafter the noise components are added to the bone image containing no noise component. However, perceptible noise components fall within a comparatively high frequency region. Therefore, from the point of view of easy calculations, a frequency response processing should preferably be carried out such that comparatively low frequency components of the bone image are reduced, and comparatively high frequency components of the bone image are kept.

The present invention also provides an apparatus for displaying an energy subtraction image, which comprises:

i) an image read-out means for reading out radiation images and converting them into digital image signals, ii) a subtracting operation means for:

after a plurality of radiation images of an object constituted of bones and soft tissues, which radiation images have been formed with at least two kinds of radiation having different energy distributions and having passed through said object and in which different images of at least part of said object are embedded, are read out by said image read-out means and converted thereby into a plurality of digital image signals, each of which is made up of a series of image signal components, subtracting the image signal components of the digital image signals from each other, which image signal components represent corresponding picture elements in the plurality of said radiation images, and thereby generating a difference signal representing a soft tissue image, in which the patterns of the bones represented by said radiation images have been erased, and a difference signal representing a bone image, in which the patterns of the soft tissues represented by said radiation images have been erased, iii) an image processing means for independently carrying out different image processing operations on said difference signal representing said soft tissue image and said difference signal representing said bone image, iv) an addition means for adding the difference signals, which have been obtained from said image processing operations, and v) a display means for reproducing a visible radiation image of said object from an image signal, which has been obtained from said addition, and displaying the reproduced image in which said soft tissue image and said bone image are superposed one upon the other.

In the method and apparatus for displaying an energy subtraction image in accordance with the present invention, radiation images may be read out with one of various methods. By way of example, radiation images may be stored on stimulable phosphor sheets. The radiation images, which have been stored on the stimulable phosphor sheets may then be read out from an image read-out operation wherein each stimulable phosphor sheet is scanned with stimulating rays, which cause it to emit light in proportion to the amount of energy stored thereon during its exposure to radiation, and the emitted light is detected photoelectrically. Alternatively, an image intensifier may be used during the operation for reading out a radiation image. As another alternative, a film digitizer may be used during the operation for reading out a radiation image.

One of the methods utilizing stimulable phosphor sheets is proposed in, for example, U.S. Pat. No. 4,590,517. In the proposed method, stimulable phosphor sheets are used, on which radiation images can be recorded even when the energy intensity of the radiation to which the stimulable phosphor sheets are exposed varies over a wide range. The stimulable phosphor sheets are exposed to radiation, which has passed through an object, under different conditions, and a plurality of radiation images, in which different images of a specific structure of the object are embedded, are thereby stored on the stimulable phosphor sheets. Each of the stimulable phosphor sheet is then exposed to stimulating rays, which cause it to emit light in proportion to the amount of energy stored thereon during its exposure to the radiation, and the emitted light is detected and converted into a digital image signal.

As disclosed in, for example, U.S. Pat. No. 4,258,264, when certain kinds of phosphors are exposed to radiation such as X-rays, $\alpha$-rays, $\beta$-rays, $\gamma$-rays, cathode rays or ultraviolet rays, they store part of the energy of the radiation. Then, when the phosphor which has been exposed to the radiation is exposed to stimulating rays such as visible light, light is emitted by the phosphor in proportion to the amount of energy stored thereon during its exposure to the radiation. A phosphor exhibiting such properties is referred to as a stimulable phosphor. A sheet provided with a layer of the stimulable phosphor is referred to as the stimulable phosphor sheet.

On stimulable phosphor sheets, images can be recorded even when the energy intensity of the radiation to which the stimulable phosphor sheets are exposed varies over a wide range. Also, the stimulable phosphor sheets provide very good resolution. Therefore, in cases where digital subtraction processing is carried out on radiation images stored on stimulable phosphor sheets, even if the radiation doses to the stimulable phosphor sheets fluctuate during the operations for recording the radiation images, a subtraction image can be obtained which has good image quality and can serve as an effective tool in, particularly, the efficient and accurate diagnosis of an illness.

As described above, in the method for displaying an energy subtraction image in accordance with the present invention, a single radiation image is displayed in which the images represented by the two difference signals obtained from the subtraction processing are superposed one upon the other. Therefore, such that the two images represented by the two difference signals may be combined compatibly, the image density (in cases where the single radiation image is displayed on a CRT display device, or the like, the luminance), or the contrast, or both the image density and the contrast of at least one of the two images should preferably be corrected in accordance with the density range, or the contrast range, or both the density range and the contrast range of the other image.

With the method for displaying an energy subtraction image in accordance with the present invention, the bone image and the soft tissue image are subjected to different image processing operations (e.g. frequency emphasis processing operations or gradation processing operations), or only one of the images is subjected to an image processing operation. Thereafter, the processed images are superposed one upon the other and displayed. Therefore, a radiation image can be displayed which has good image quality and can serve as an effective tool in, particularly, the efficient and accurate diagnosis of an illness, and in which both the bone patterns and the soft tissue patterns are included.

In cases where frequency emphasis processing operations wherein emphasis coefficients are equal and only the mask sizes are different are carried out on the bone image and the soft tissue image, the processed images can be superposed one upon the other and displayed such that noise is imperceptible visually. Therefore, a radiation image can be displayed which has good image quality and can serve as an effective tool in, particularly, the efficient and accurate diagnosis of an illness.

Heretofore, when the patterns of soft tissues are to be observed, because the patterns of bones adversely affect the observation, a radiation image recorded with radiation having a high energy level, or a soft tissue image obtained from energy subtraction processing has been observed. However, in a radiation image recorded with radiation having a high energy level, even though the contrast of the bone patterns becomes low, the contrast of the soft tissue patterns also becomes low. Therefore, such a radiation image is indistinct. Also, with a soft tissue image, in which the bone patterns have been erased, the problem occurs in that the relationship between the positions of the soft tissue patterns and the bone patterns cannot be found easily. Additionally, a soft tissue image contains many noise components. Therefore, the soft tissue image is rough and indistinct.

As described above, with the method for displaying an energy subtraction image in accordance with the present invention, the difference signal representing the bone image can be processed such that noise components contained in the bone image are kept and the contrast of the bone patterns is reduced. Thereafter, the difference signals, which represent the bone image and the soft tissue image and which have been obtained from the image processing operations, are added together. In such cases, in a visible radiation image reproduced from an image signal, which has been obtained from the addition, bone patterns having low contrast can be superposed upon the soft tissue image. Also, the visible radiation image thus reproduced contains little noise and is suitable for the observation of soft tissue patterns.

Also, when the frequency response processing, wherein comparatively low frequency components of the bone image are reduced, and comparatively high frequency components of the bone image are kept, is employed as the process for keeping noise components contained in the bone image and reducing the contrast of the bone patterns, a visible radiation image suitable for the observation of soft tissue patterns can be obtained with simple processing.

DESCRIPTION OF THE PREFERRED EMBODIMENTS

The present invention will hereinbelow be described in further detail with reference to the accompanying drawings.

Figure 1A:
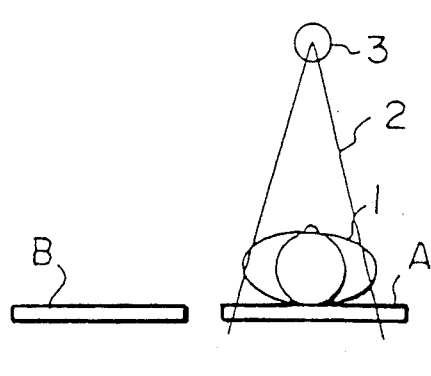
FIGS. 1A and 1B are explanatory views showing examples of the steps for recording radiation images in embodiments of the method for displaying an energy subtraction image in accordance with the present invention.

With reference to FIG. 1A, stimulable phosphor sheets A and B are sequentially exposed to X-rays 2, which have passed through an object 1 constituted of bones and soft tissues, such as the lung fields and blood vessels, and which have different energy levels. Specifically, first, an X-ray image of the object 1 is stored on the stimulable phosphor sheet A. Thereafter, the stimulable phosphor sheet A is quickly removed from the position for exposure to the X-rays 2, and the stimulable phosphor sheet B is quickly set at the position for exposure to the X-rays 2. At the same time, the tube voltage of the X-ray source 3 is changed so that it produces the X-rays 2 having a different energy level. In this manner, an X-ray image of the object 1 is stored on the stimulable phosphor sheet B with the X-rays 2 having the different energy level. The positions of the stimulable phosphor sheets A and B with respect to the position of the object 1 are kept the same.

Figure 1B:
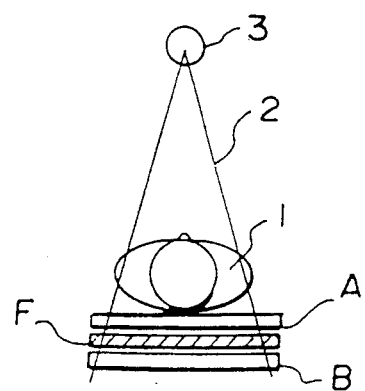

Alternatively, an image recording operation may be carried out in the manner shown in FIG. 1B. With reference to FIG. 1B, stimulable phosphor sheets A and B are placed one upon the other, and a filter F capable of absorbing part of radiation energy is inserted between the stimulable phosphor sheets A and B. The stimulable phosphor sheets A and B are exposed to X-rays 2, which have passed through an object 1. In this manner, the stimulable phosphor sheets A and B are simultaneously exposed to the X-rays 2 having different energy levels. The image recording operation is thus carried out for one-shot energy subtraction processing. One of one-shot energy subtraction processing methods is disclosed in, for example, U.S. Pat. No. 4,855,598.

Figure 2:
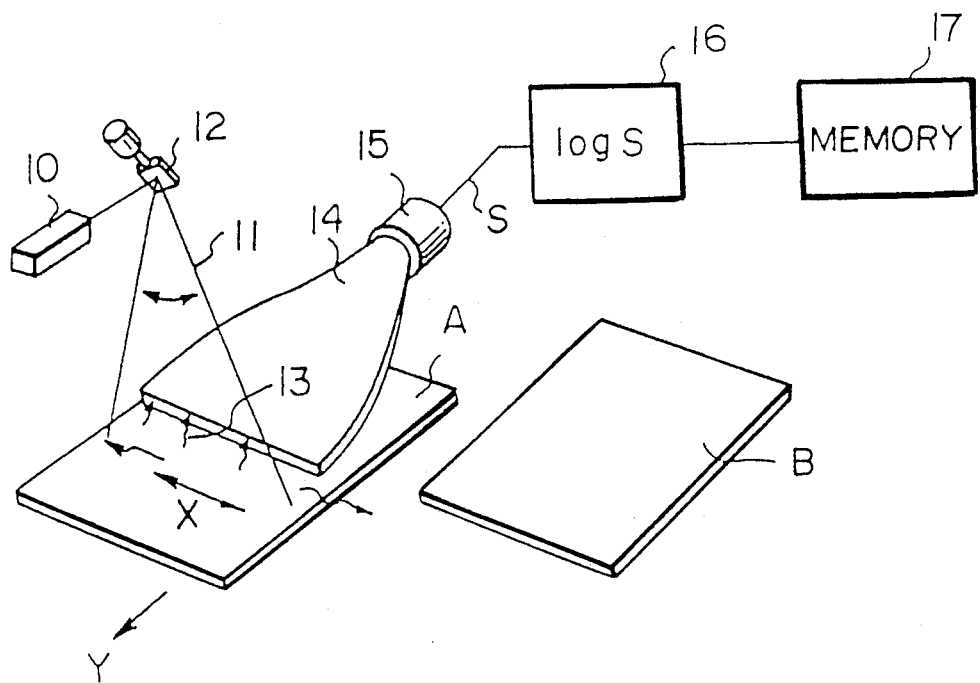
FIG. 2 is a schematic view showing how radiation images are read out from stimulable phosphor sheets.

In the manner described above, two X-ray images, in which different images of at least part of the object 1 are embedded, are stored on the stimulable phosphor sheets A and B. Thereafter, in an image read-out means shown in FIG. 2, the X-ray images are read out from the stimulable phosphor sheets A and B, and digital image signals representing the X-ray images are thereby obtained. Specifically, first, the stimulable phosphor sheet A is moved in the sub-scanning direction indicated by the arrow Y. At the same time, a laser beam 11, which serves as stimulating rays, is produced by a laser beam source 10. The laser beam 11 is deflected by a scanning mirror 12 and caused to scan the stimulable phosphor sheet A in the main scanning directions indicated by the double-headed arrow X. When the stimulable phosphor sheet A is exposed to the laser beam 11, it emits light 13 in proportion to the amount of energy stored thereon during its exposure to the X-rays 2. The emitted light 13 enters a light guide member 14, which is made from a transparent acrylic plate, from its one edge face. The emitted light 13 is guided through repeated total reflection inside of the light guide member 14 and detected by a photomultiplier 15. The photomultiplier 15 generates an image signal S corresponding to the amount of the emitted light 13, i.e. representing the X-ray image stored on the stimulable phosphor sheet A.

The image signal S is converted into a digital image signal logSA having logarithmic values (logS) by a logarithmic converter 16 provided with an amplifier and an A/D converter. The digital image signal logSA is stored on a storage medium 17, such as a magnetic disk. Thereafter, the X-ray image stored on the stimulable phosphor sheet B is read out in the same manner as that described above. The digital image signal logSB representing the X-ray image stored on the stimulable phosphor sheet B is stored on the storage medium 17.

Thereafter, subtraction processing is carried out on the digital image signals logSA and logSB, which have been obtained in the manner described above.

Figure 3:
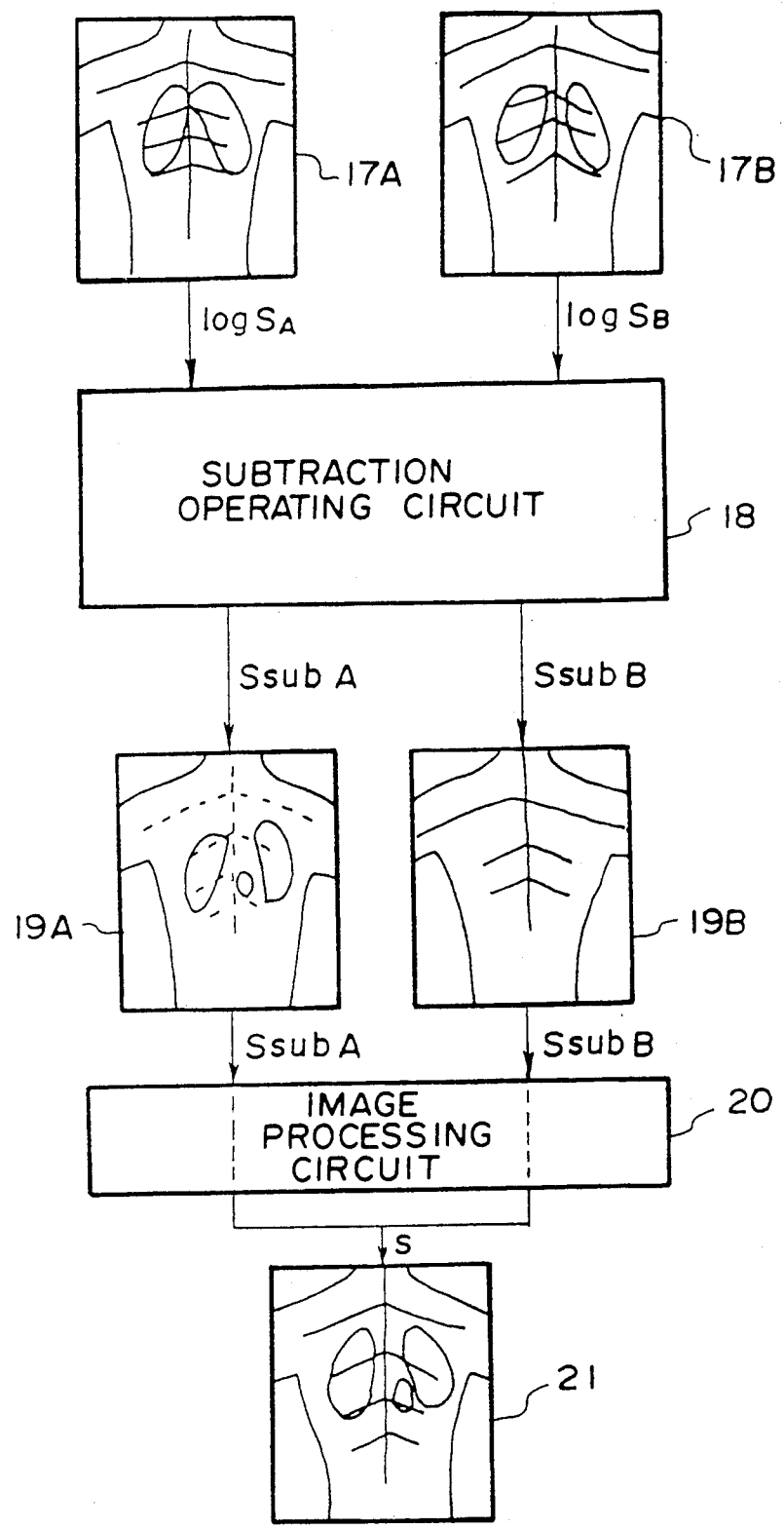
FIG. 3 is an explanatory block diagram showing how energy subtraction processing is carried out in an embodiment of the method for displaying an energy subtraction image in accordance with the present invention.

FIG. 3 shows the flow of signals in an embodiment of the method for displaying an energy subtraction image in accordance with the present invention. With reference to FIG. 3, the digital image signals logSA and logSB are read from image files 17A and 17B on the storage medium 17 and fed into a subtraction operating circuit 18. The subtraction operating circuit 18 appropriately weights the digital image signals logSA and logSB. Thereafter, the subtraction operating circuit 18 subtracts the image signal components of the digital image signals logSA and logSB from each other which represent corresponding picture elements in the two X-ray images. From the subtraction processing, a digital difference signal is obtained, which is expressed as $$Ssub = a \cdot logSA - b \cdot logSB + c$$

wherein a and b denote weighting coefficients, and c denotes a bias component for adjusting such that the image density represented by the difference signal Ssub becomes approximately equal to a predetermined level.

Figure 4A:
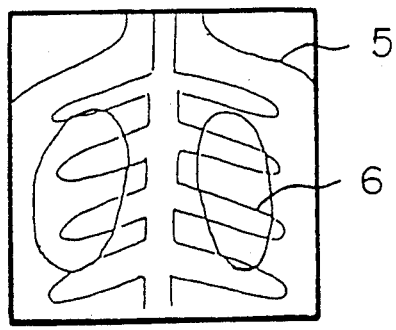
FIGS. 4A, 4B, and 4C are explanatory views showing examples of an original image and images obtained from energy subtraction processing.
Figure 4B:
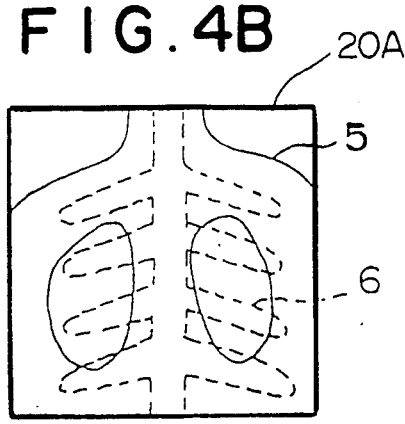
Figure 4C:
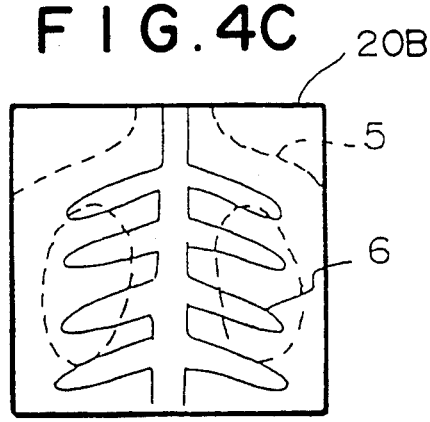

By way of example, in the cases of X-ray images of the chest of a human body, a digital image signal logSA detected from an image A, which was recorded with the X-rays having a high energy level, is stored in the image file 17A. Also, a digital image signal logSB detected from an image B, which was recorded with the X-rays having a low energy level, is stored in the image file 17B. The digital image signals logSA and logSB are read from the image files 17A and 17B, and two subtraction images are formed from the digital image signals logSA and logSB. Specifically, as shown in FIG. 4A, the X-ray images of the object 1, which are represented by the digital image signals logSA and logSB stored in the image files 17A and 17B, are composed of, for example, soft tissue patterns 5 and bone patterns 6. In such cases, the subtraction operating circuit 18 carries out subtraction processing, which is expressed as $$Ssub = a \cdot logSA - b \cdot logSB + c$$

wherein a and b denote weighting coefficients, and c denotes a bias component for adjusting such that the image density represented by the difference signal Ssub becomes approximately equal to a predetermined level. By appropriately selecting the weighting coefficients a and b, an image signal SsubA is obtained which represents a soft tissue image 20A shown in FIG. 4B. In the soft tissue image 20A, the bone patterns 6 have been erased, and only the soft tissue patterns 5 are present. Also, an image signal SsubB is obtained which represents a bone image 20B shown in FIG. 4C. In the bone image 20B, the soft tissue patterns 5 have been erased, and only the bone patterns 6 are present.

The image signals SsubA and SsubB are stored in files 19A and 19B and thereafter fed into an image processing circuit 20. The image processing circuit 20 carries out appropriate image processing operations on the soft tissue image 20A and/or the bone image 20B. The image signals obtained from the image processing operations are then added together, and an image signal S is thereby obtained. Thereafter, the image signal S is fed into an image display device 21, such as a CRT display device. An image is reproduced from the image signal S and displayed on the image display device 21. The image displayed on the image display device 21 is composed of the soft tissue image 20A and the bone image 20B which have been processed appropriately. In this manner, by way of example, a pattern of a diseased part in the soft tissue image 20A can be observed with the bone image 20B serving as a background such that the relationship between the pattern of the diseased part and the bone image 20B can be found clearly. Therefore, the position of the pattern of the diseased part can be found more reliably (particularly, with respect to the position of bone patterns) than when only the soft tissue image 20A is displayed. Accordingly, an image can be observed which has good image quality and can serve as an effective tool in, particularly, the efficient and accurate diagnosis of an illness.

For example, when patterns of lumps in the lung fields are to be emphasized in an image of the chest, an image processing operation for emphasizing the high frequency components is carried out on the soft tissue image 20A, and no image processing operation is carried out on the bone image 20B. Thereafter, a visible image is reproduced in which the two images are superposed one upon the other. In this manner, an image can be displayed in which the bone patterns are imperceptible and a soft tissue image, whose high frequency components have been emphasized, is shown with the bone patterns serving as the background. Therefore, an image can be displayed which has good image quality and can serve as an effective tool in, particularly, the efficient and accurate diagnosis of an illness.

However, when the image processing is carried out in the manner described above, there is the risk that noise components are also emphasized. Therefore, the technique described below is employed in order to yield an image in which the noise components are minimized, the bone patterns are imperceptible, and the positions of the bone patterns can be found.

Figure 5:
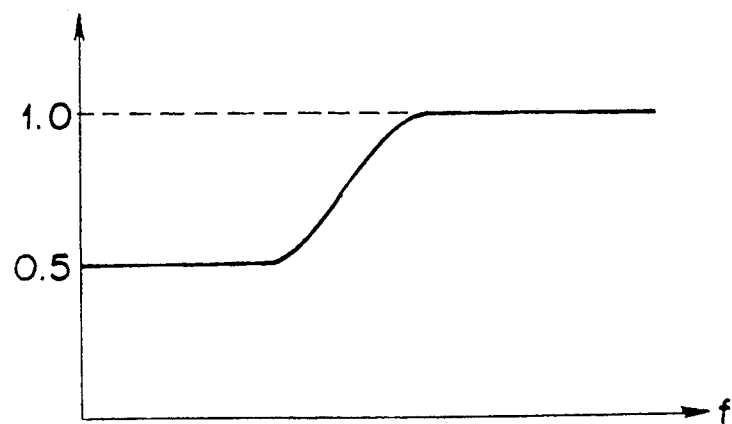
FIG. 5 is a graph showing the filtering characteristics of image processing carried out on a bone image.

First, a signal B' representing a bone image, which has been processed, is calculated from the formula $$B' = \{B + (B - Bu)\}/2 \qquad (2)$$

wherein B denotes a difference signal representing the bone image, and Bu denotes the mean value of the values of image signal components representing $M^2$ number of picture elements of the bone image, i.e. a group of picture elements arrayed along M number of rows and M number of columns. The operation carried out with Formula (2) corresponds to the operation carried out with Formula (1) wherein $\beta$ is set to 1.0 (i.e. emphasis coefficient is equal to 1.0) and the calculated value is multiplied by $\frac{1}{2}$. As for the low frequency components, B is approximately equal to Bu, and therefore the formula, $B' = B/2$, obtains. As for the high frequency components, Bu is approximately equal to 0 (zero), and therefore the formula, $B' = B$, obtains. Specifically, as shown in FIG. 5, the operation carried out with Formula (2) corresponds to the filtering operation in which the response to the high frequency range is equal to 1.0 and the response to the low frequency components is decreased to 0.5.

By adding the signal B', which has been obtained with Formula (2), to the difference signal representing the soft tissue image, a soft tissue image can be obtained in which the noise components have been minimized and the bone patterns having low contrast are contained.

The contrast of the bone patterns can be adjusted with, for example, the operation expressed as $$B' = \{B + 2 \cdot (B - Bu)\}/3 \qquad (3)$$

In general, the contrast of the bone patterns can be adjusted arbitrarily with the operation expressed as $$B' = \{B + n \cdot (B - Bu)\}/(n + 1) \qquad (4)$$

Also, processing equivalent to Formulas (2), (3), and (4) can be effected by carrying out Fourier transformation on the difference signal representing the bone image, carrying out the process for reducing the low frequency components as shown in FIG. 5 in the frequency space, and thereafter carrying out inverse Fourier transformation.

In the manner described above, the contrast of the bone patterns can be reduced as if they were in an X-ray image recorded with X-rays having a high energy level, such that the noise components do not increase (i.e. the graininess is not adversely affected) and the contrast of the soft tissue patterns is kept unchanged. Therefore, it becomes unnecessary for an expensive or special X-ray generating device, which produces X-rays having a high energy level, to be used.

As another example, in cases where the pattern of a thighbone or the ridge of a bone is to be emphasized, an image processing operation for emphasizing the high frequency region may be carried out on the bone image 20B, and no image processing operation is carried out on the soft tissue image. Thereafter, an image is displayed in which the two images are superposed one upon the other. In this manner, a bone image in which the ridge of the bone has been emphasized can be displayed together with an imperceptible soft tissue image.

As described above, in cases where frequency emphasis processing operations are employed as the image processing operations, the operations should preferably be carried out such that the emphasis coefficients are equal and only the mask sizes are changed for the bone image and the soft tissue image. From such operations, a combined image can be obtained in which noise is visually imperceptible.

Operations for subtraction processing and a parameter used for the subtraction processing will be described hereinbelow.

X-ray absorption coefficients $\mu$ are classified into the following:

$\mu LT$: Absorption coefficient of soft tissues with respect to X-rays having a low energy level.

$\mu HT$: Absorption coefficient of soft tissues with respect to X-rays having a high energy level.

$\mu LB$: Absorption coefficient of bones with respect to X-rays having a low energy level.

$\mu HB$: Absorption coefficient of bones with respect to X-rays having a high energy level.

When the image recorded with X-rays having a high energy level is represented by logSA, and the image recorded with X-rays having a low energy level is represented by logSB, a signal SsubA representing the soft tissue image 20A can be obtained from the subtracting operations expressed as $$SsubA = \frac{\mu LB}{\mu HB} \log SA - \log SB$$

Also, a signal SsubB representing the bone image 20B can be obtained from the subtracting operations expressed as $$SsubB = \log SB - \frac{\mu LT}{\mu HT} \log SB$$

In this embodiment, image processing operations are carried out on the signals SsubA and SsubB, and signals SsubA' and SsubB' are obtained from the image processing operations. The signals SsubA' and SsubB' are then superposed one upon the other. The superposition is expressed as $$SA = (SsubA' + SsubB')/\left(\frac{\mu LB}{\mu HB} - \frac{\mu LT}{\mu HT}\right) \quad (5)$$

or $$SB = \left(\frac{\mu LT}{\mu HT} \times SsubA' + \frac{\mu LB}{\mu HB} \times SsubB'\right)/ \quad (6)$$

$$\left(\frac{\mu LB}{\mu HB} - \frac{\mu LT}{\mu HT}\right)$$

When no image processing operation is carried out, the superposed signal SA calculated with Formula (5) corresponds to the signal SsubA. Also, when no image processing operation is carried out, the superposed signal SB calculated with Formula (6) corresponds to the signal SsubB.

An image represented by the superposed signal SA or SB or a signal calculated with the formula (SA+SB)/2 is then displayed. When the image represented by the signal calculated with the formula (SA+SB)/2 is displayed, noise reducing effects can be obtained.

During the energy subtraction processing, the configuration of the stimulable phosphor sheets, the way in which the stimulable phosphor sheets are moved, or the like, may be selected from known techniques.

Correction of the image density and/or the contrast may be carried out only for one of the difference signals SsubA and SsubB or for both of them. Such correction need not necessarily be carried out. However, when the correction is carried out, the images represented by the corrected signals become combined compatibly.

In the aforesaid embodiment, radiation images are stored on the stimulable phosphor sheets and read out therefrom. Alternatively, radiation images may be detected by using an image intensifier. As another alternative, images recorded on sheets of film may be converted into digital image signals by using a film digitizer. No limitation is imposed on how radiation images are detected insofar as digital image signals are obtained.

The energy subtraction processing wherein stimulable phosphor sheets are used is also applicable when, for example, a subtraction image in which a pattern of a medical implement has been erased is to be obtained from radiation images of a human body having the medical implement embedded therein, and when a subtraction image in which a pattern of contrast media has been erased is to be obtained from radiation images of a human body injected with contrast media. Accordingly, the term "bone" as used herein embraces metals, contrast media, and other materials which can be regarded as elements equivalent to bones from the point of view of signal processing. Also, the term "soft tissue" as used herein embraces various substances which exhibit different radiation absorption characteristics from bones and elements equivalent to bones, and the patterns of which can be extracted from radiation images by the energy subtraction processing.

I claim:

1. A method for displaying an energy subtraction image during energy subtraction processing wherein a plurality of radiation images of an object constituted of bones and soft tissues, which radiation images have been formed with at least two kinds of radiation having different energy distributions and having passed through the object and in which different images of at least part of the object are embedded, are read out and converted into a plurality of digital image signals, each of which is made up of a series of image signal components, the image signal components of the digital image signals which represent corresponding picture elements in the plurality of the radiation images are then subtracted from each other, and a difference signal representing a soft tissue image, in which the patterns of the bones represented by the radiation images have been erased, and a difference signal representing a bone image, in which the patterns of the soft tissues represented by the radiation images have been erased, are thereby obtained, the method for displaying an energy subtraction image comprising the steps of:
i) carrying out different image processing operations on said difference signal representing said soft tissue image and said difference signal representing said bone image,
ii) adding the difference signals, which have been obtained from said image processing operations, and iii) reproducing a visible radiation image of said object from an image signal, which has been obtained from said addition.

2. A method as defined in claim 1 wherein said different image processing operations are frequency emphasis processing operations wherein emphasis coefficients are equal and mask sizes are different.

3. A method as defined in claim 1 wherein an image processing operation, which is carried out on said difference signal representing said bone image, includes a process with which noise components contained in said bone image are kept and contrast of said bone patterns is reduced.

4. A method as defined in claim 3 wherein said process, with which noise components contained in said bone image are kept and contrast of said bone patterns is reduced, is a frequency response processing with which comparatively low frequency components of said bone image are reduced, and comparatively high frequency components of said bone image are kept.

5. A method as defined in claim 1 wherein said radiation images have been stored on stimulable phosphor sheets.

6. A method as defined in claim 5 wherein said radiation images stored on said stimulable phosphor sheets are read out from an image read-out operation in which each said stimulable phosphor sheet is exposed to stimulating rays, which cause it to emit light in proportion to the amount of energy stored thereon during its exposure to radiation, and the emitted light is detected photoelectrically.

7. A method as defined in claim 6 wherein said stimulating rays are a laser beam.

8. An apparatus for displaying an energy subtraction image, which comprises:
   i) an image read-out means for reading out radiation images and converting them into digital image signals,
   ii) a subtracting operation means for:
      after a plurality of radiation images of an object constituted of bones and soft tissues, which radiation images have been formed with at least two kinds of radiation having different energy distributions and having passed through said object and in which different images of at least part of said object are embedded, are read out by said image read-out means and converted thereby into a plurality of digital image signals, each of which is made up of a series of image signal components,
      subtracting the image signal components of the digital image signals from each other, which image signal components represent corresponding picture elements in the plurality of said radiation images, and thereby generating a difference signal representing a soft tissue image, in which the patterns of the bones represented by said radiation images have been erased, and a difference signal representing a bone image, in which the patterns of the soft tissues represented by said radiation images have been erased,
   iii) an image processing means for independently carrying out different image processing operations on said difference signal representing said soft tissue image and said difference signal representing said bone image,
   iv) an addition means for adding the difference signals, which have been obtained from said image processing operations, and
   v) a display means for reproducing a visible radiation image of said object from an image signal, which has been obtained from said addition, and displaying the reproduced image in which said soft tissue image and said bone image are superposed one upon the other.

9. An apparatus as defined in claim 8 wherein said different image processing operations are frequency emphasis processing operations wherein emphasis coefficients are equal and mask sizes are different.

10. An apparatus as defined in claim 8 wherein an image processing operation, which is carried out on said difference signal representing said bone image, includes a process with which noise components contained in said bone image are kept and contrast of said bone patterns is reduced.

11. An apparatus as defined in claim 10 wherein said process, with which noise components contained in said bone image are kept and contrast of said bone patterns is reduced, is a frequency response processing with which comparatively low frequency components of said bone image are reduced, and comparatively high frequency components of said bone image are kept.

12. An apparatus as defined in claim 8 wherein said radiation images have been stored on stimulable phosphor sheets.

13. An apparatus as defined in claim 12 wherein said image read-out means reads out each of said radiation images stored on said stimulable phosphor sheets from an image read-out operation in which each said stimulable phosphor sheet is exposed to stimulating rays, which cause it to emit light in proportion to the amount of energy stored thereon during its exposure to radiation, and the emitted light is detected photoelectrically.

14. An apparatus as defined in claim 13 wherein said stimulating rays are a laser beam.

* * * * *